United States Patent [19]

Vyas et al.

[11] Patent Number: 5,776,711
[45] Date of Patent: Jul. 7, 1998

[54] SIMULTANEOUS HUMAN ABO AND RH(D) BLOOD TYPING OR ANTIBODY SCREENING BY FLOW CYTOMETRY

[75] Inventors: Girish N. Vyas; Kodumudi Venkateswaran, both of San Francisco, Calif.

[73] Assignee: The Regents of the University of California, Oakland, Calif.

[21] Appl. No.: 747,558

[22] Filed: Nov. 12, 1996

[51] Int. Cl.$^6$ .................. G01N 33/53; G01N 33/555
[52] U.S. Cl. .................. 435/7.25; 435/2; 435/7.21; 604/7
[58] Field of Search .................. 436/533, 534, 436/523, 501; 435/2, 7.21, 7.25; 604/7

[56] References Cited

U.S. PATENT DOCUMENTS

| | | |
|---|---|---|
| 4,550,017 | 10/1985 | Liu et al. . |
| 4,584,277 | 4/1986 | Ullman . |
| 4,748,129 | 5/1988 | Chang et al. . |
| 4,751,188 | 6/1988 | Valet . |
| 5,567,627 | 10/1996 | Lehnen . |

FOREIGN PATENT DOCUMENTS

WO 93/02360  2/1993  WIPO .

OTHER PUBLICATIONS

Aminololama–Shakeri, S., et al., "Simultaneous ABO and Rh Blood Typing by Flow Cytometry Using a Three Color Fluorescence Detection System," (1995) *Blood* 86 (10): 609a.

Chung, A., et al., "A Microplate System for ABO and Rh(D) Blood Grouping," (1993) *Transfusion* 33 (5):384–388.

Freedman, J., and Lazarus, A.H., "Applications of Flow Cytometry in Transfusion Medicine," *Transfusion Med. Rev.* 9 (2):87–109.

Fulwyler, M.J. and McHugh, T.M., "Flow Microsphere Immunoassay for the Quantitative and Simultaneous Detection of Multiple Soluble Analytes," (1990) *Methods Cell Biol.* 33:613–629.

Garratty, G., and Arndt, P., "Applications of Flow Cytofluorometry to Transfusion Science," (1995) *Transfusion* 35 (1):157–178.

Giblett, E.R., "Blood Groups and Blood Transfusion," in: Harrison's Principles of Internal Medicine, 12th Edition, Wilson, J.D. et al. (eds.), McGraw–Hill, Inc., New York, 1991, pp. 1494–1500.

Growe, G.H., et al., "The Implementation and Use of Automated group and Screen Procedures in a Hospital Transfusion Laboratory," (1996) *Transfusion Med. Rev.* 10 (2):144–151.

Lapierre, Y., et al., "The Gel Test: A New Way to Detect Red Cell Antigen–Antibody Reactions," (1990) *Transfusion* 30 (1): 109–113.

Scillian, J.J., et al., "Early Detection of Antibodies Against rDNA–produced HIV Proteins with a Flow Cytometric Assay," (1989) *Blood* 73 (7): (2041–2048.

Scott, M.L.,"The Principles and Applications of Solid–phase Blood Group Serology," (1991) *Transfusion Med. Rev.* 5 (1):60–72.

Uthemann, H., and Poschmann, A., "Solid–phase Antiglobulin Test for Screening and Identification and Red Cell Antibodies," (1990) *Transfusion* 30 (2):114–116.

Yang, G., et al., "Flow Cytometric Detection of Human Immuno–deficiency Virus Type 1 Proviral DNA by the Polymerase Chain Reaction Incorporating Digoxigenin–or Fluorescein–labeled dUTP," (1995) *Cytometry* 21 (1):197–202.

Scornik, *Cytometry*, vol. 22, No. 4, pp. 259–263, 1995.

*Primary Examiner*—Toni R. Scheiner
*Attorney, Agent, or Firm*—Bozicevic & Reed LLP; Karl Bozicevic, Esq.

[57] ABSTRACT

Flow cytometric methodology is provided for simultaneous determination of (1) ABO and Rh(D) typing of human red cells, (2) natural isoantibodies in plasma, and (3) screening for alloantibodies in plasma. The method includes (a) the use of a unique combination of fluorescent labelled antibodies to A, B and Rh(D) antigens to carry out (1); (b) different sized beads coated with blood group substances A & B to carry out (2); and (c) the differential fluorescent labelling of screening reagent red blood cells for flow cytometric analyses to carry out (3). The routine ABO and Rh(D) typing and antibody screening of human blood for both isoantibodies and alloantibodies can be determined in three individual reactions compared to 7 to 10 tests currently performed in blood banks.

18 Claims, 4 Drawing Sheets

Forward (x-axis) vs side scatter (y-axis)

Conclusion: Cells are Red Blood cells

FIG. 1A

Rh (subtyping)
A (x-axis) vs Rh (y-axis)

Conclusion:
x-axis: A negative
y-axis: Rh negative

FIG. 1B

ABO typing
A (x-axis) vs B (y-axis)

Conclusion:
x-axis: A negative
y-axis: B negative

FIG. 1C

Forward (x-axis) vs side scatter (y-axis)

Conclusion: Cells are Red Blood cells

FIG. 2A

Rh (subtyping)
A (x-axis) vs Rh (y-axis)

Conclusion:
x-axis: A positive
y-axis: Rh positive

FIG. 2B

ABO typing
A (x-axis) vs B (y-axis)

Conclusion:
x-axis: A positive
y-axis: B positive

SIMULTANEOUS HUMAN ABO AND RH(D) BLOOD TYPING OR ANTIBODY SCREENING BY FLOW CYTOMETRY

TECHNICAL FIELD

The present invention relates to flow cytometric methods for the simultaneous detection of ABO and Rh(D) antigens in human red blood cells (RBC), isoantibodies to erythrocyte antigens A and B in serum/plasma, and alloimmune antibodies of clinical significance to blood group antigens in serum/plasma.

BACKGROUND OF THE INVENTION

Annually, about 14 million voluntary blood donations and about 8 million platletapheresis are performed in the United States of America. Before this blood can be used it must be tested for ABO and Rh(D) blood groups and screened for alloimmune antibodies. Current methods in blood centers employ agglutination assays and about 7 to 10 individual reactions are required to arrive at the results for each blood sample. To determine the blood group, red blood cells are reacted separately with anti-A, anti-B, anti-AB and anti-D antibodies. The serum/plasma from the same blood sample is also individually tested with Type A and Type B reagent RBCs and at least two different pools of Type O reagent cells representing most of the antigens of clinical significance. Thus, in the U.S. alone 150 to 200 million tests are performed annually to determine the blood groups in blood centers.

It is therefore of interest to develop a method which would make it possible for a blood bank technologist to simultaneously determine blood group antigens in the red cells as well as antibodies of clinical significance in the serum. Such a method would considerably decrease the number of individual tests performed i.e., provide a reduction of about 50 to 100 million tests per year in the number of tests performed in blood centers resulting in significant savings of time and cost.

RELEVANT LITERATURE

Millions of blood samples are routinely screened for ABO and Rh(D) blood groups by hemagglutination test to detect the presence of antigens on red blood cells (RBCs) and antibodies in serum. These tests are based on Landsteiner's seminal experiments at the turn of the century. Landsteiner, *Science* 73:405 (1931) and on the work of Ashby, *J. Exp. Med.* 29:267 (1919) and Coombs *Brit. J. Exp. Pathol.* 26:255 (1945). The results of manual agglutination tests conducted in liquid phase are subjective and require considerable expertise and technical skills for interpretation. Instead of using tubes or tiles, large scale blood typing has been carried out in microplates without any fundamental change in technique since a microplate is a block of 96 small tubes (Uthemann and Poschmann, 1990). The advantages of blood grouping in microplates include easier manipulation of large numbers of samples, objective measurement of agglutination reactions using instruments and computer interfacing for compilation and management of results. A number of expensive and dedicated systems with computer-controlled robotics and high throughput spectrophotometric readers have been introduced for blood bank automation (Chung, et al., *Transfusion* 33:384 (1992).

Commercial blood typing kits have been introduced with improved detection of red cell antigen and antibody reactions in special microtubes filled with reagents in gel form, Lapierre, et al., *Transfusion* 30:109 (1990). Utility of solid-phase techniques to overcome the inherent problems in the use of hemagglutination as an end point for blood grouping was reviewed by Scott *Transfusion Med. Rev.* 5:60 (1991). Recently Growe, et al., *Transfusion Med. Rev.* 10:44 (1996) reported the implementation and use of automated grouping of RBC antigen and serum antibody screening procedures applicable not only to blood centers but also for hospital transfusion laboratories. At least seven different wells with specific typing reagents have to be used in these methods for determining the blood group of a sample. All of the procedures used for large scale blood grouping essentially employed the agglutination based methods and also for the determination of only one antigen or antibody type in a single tube/well. Separately identifiable reactions using fluorescent labeled reagents have also been reported for blood typing applications in the U.S. Pat. Nos. 4,550,017 and 4,748,129.

Flow cytometry has been used with increasing regularity in clinical laboratories for immunophenotyping of leukocyte antigens. The advantages of flow cytometry include speed, sensitivity, precision and objectivity. Garratty and Arndt, *Transfusion* 35:157 (1994) reviewed the successful use of flow cytometry in wide-ranging research applications in transfusion science. Freedman and Lazarus, *Transfusion Med. Rev.* 9:87 (1995) detailed the increasing use of flow cytometry in transfusion medicine and emphasized the need for implementing the power of this technology for more widespread application to specific immunohematologic problems.

The unique advantage of simultaneous detection of multiple analytes using different size microspheres in flow cytometry was exploited by Scillian, et al., *Blood* 73:2041 (1989) for the early edition of IgM and IgG antibodies to HIV proteins in serum. A computer-controlled robotic sample processing system has been developed. The system includes the use of microsphere-based stable reagents for automated flow cytometric screening of multiple analytes in blood (Lehnen and Crothers in WO93/02360 and U.S. Pat. No. 5,567,627). More recently, there has been a disclosure of a novel three color flow cytometric method for simultaneous ABO and Rh blood typing in a single tube, Aminololama-Shakeri, et al., *Blood* 86:609a (1995).

SUMMARY OF THE INVENTION

Flow cytometric blood typing and serum antibody screening for the expected anti-A, anti-B and any unexpected antibodies of clinical significance is carried out via one, two or three analyses rather than the 7 to 10 separate reactions required by the current immunohematological practice. The invention uses flow cytometric methods for (1) simultaneous three color ABO and Rh antigen detection in a first analysis; (2) concurrent determination of anti-A and anti-B antibodies in a second analysis; and (3) the screening of serum for the presence of unexpected antibodies with two selected pools of group O reagent RBCs in a third analysis.

An object of the invention is to provide a method for quickly and efficiently analyzing human blood samples.

Another object of the invention is to provide a method whereby only one, two or three specific analyses need be carried out in order to analyze a human blood sample.

An advantage of the invention is that the invention uses flow cytometry in a manner which provides concurrent multiple antigen and antibody analysis of a single undivided sample.

Another advantage of the invention is that the methodology is provided via integrated flow cytometric methodology which is readily amenable to automation and computerization for data evaluation utilizing suitable software.

A feature of the invention is that red blood cells are analyzed to provide results in terms of (1) ABO and Rh antigen detection; (2) anti-A and anti-B antibody determination; and (3) a determination of unexpected antibodies of clinical significance within two selected pools of group O reagent RBCs.

These and other objects, advantages and features of the present invention will become apparent to those skilled in the art upon reading the details and description of the invention as set forth herein.

BRIEF DESCRIPTION OF THE DRAWINGS

FIG. 1 shows graphic representations of three color flow cytometric simultaneous ABO and Rh antigen typing. Panel A illustrates the forward scatter and side scatter of the red blood cells from O negative blood. Panel B illustrates Rh subtyping in O negative blood. Panel C indicates ABO typing in O negative blood.

FIG. 2 shows graphic representations of three color flow cytometric simulations ABO and Rh antigen typing. Panel A illustrates the forward scatter and side scatter of the red blood cells from AB positive blood. Panel B illustrates Rh subtyping in Ab positive blood. Panel C indicates ABO typing in AB positive blood.

FIG. 3 shows graphic representations of the binding of labelled antibody to uncoated beads. Panel A is a two parameter contour plot showing the side scatter and forward scatter of the bead population. Panel B is a two parameter contour plot illustrating the absence of anti-A fluorescence (y-axis) and showing gates. Panel C is a graphic representation of the fluorescence histogram of unconjugated beads stained with anti-A fluorescently labelled antibody. No positive signal is indicated in the region labelled M.

FIG. 4 shows graphic representations of the binding of labelled antibody to beads coated with blood group substance A. Panel A is a two-parameter contour plot showing the side scatter and forward scatter of the bead population. Panel B is a two parameter contour plot illustrating the presence of anti-A fluorescence and showing gates. Panel C is a graphic representation of the fluorescence histogram of blood group substance A-coated beads stained with anti-A fluorescently labelled antibody. A positive signal is detected in the region labelled M.

DETAILED DESCRIPTION OF THE PREFERRED EMBODIMENTS

Before the present blood assay materials and methods of using such are described, it is to be understood that this invention is not limited to the particular materials, methods, or processes described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and," and "the" include plural references unless the contexts clearly dictates otherwise. Thus, for example, reference to "a blood sample" includes mixtures and large numbers of such samples, reference to "an analysis" includes large numbers of such, and reference to "the label" includes one or more labels of the type described herein.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited in connection with.

DEFINITIONS

By "blood transfusion" is meant the introduction of whole blood or blood component directly into the blood stream. As considerable morbidity, and to a lesser extent mortality, can be associated with blood transfusion procedures, sufficient background information must be known to determine what blood components, type, and quantity are needed (see Blood Transfusion Therapy, A Physician's Handbook, 3rd Edition, American Association of Blood Banks, 1989, herein incorporated by reference, and Giblett, E. R. "Blood Groups and Blood Transfusion" In: Harrison's Principles of Internal Medicine, 12th Edition, Wison, J. D. et al. (eds), McGraw-Hill, Inc. New York, 1991, pp. 1494–1500, herein incorporated by reference).

Human red blood cell membranes contain over 300 different antigenic determinants, the molecular structure of which is dictated by genes at an unknown number of chromosomal loci. The term "blood group" is applied to any well-defined system of red blood cell antigens controlled by a locus having a variable number of allelic genes, such as A,B,O in the ABO system. Twenty-one blood groups are currently recognized (Giblet, E. R. "Blood Group Antigens and Antibodies" In: Harrison's Principle of Internal Medicine, 10th Edition, Petersdorf, R. G. et al (eds.) McGraw-Hill Book Co., New York, pp.1909–1916).

The term "blood type" refers to the antigen phenotype, which is the serologic expression of the inherited blood group genes.

The term "ABO system" means an allelic blood group system which contains four major allelic genes: $A^1$, $A^2$, B, and O. The locus for these alleles is on chromosome 9. The actual products of the first three genes are glycosyltransferases which select specific sugars, and attach them by alpha-linkage to short (oligo) saccharide chains. The O gene product is a protein which cross-reacts immunologically with the A and B transferase antibodies but has no detectable enzyme activity; thus it is functionally silent.

"Rh" phenotypes are a serologically described set of antigenic components. The underlying biochemical genetics are unknown. The Rh locus is on chromosome 1. It is generally thought that there are three anti-helical determinants in the Rh locus, termed "C" (or "c"), "E" (or "e") and "D" (or "d") (Giblet, E. R. supra). The $D(Rh_o)$ antigen is the most immunogenic of this or any other blood group system. About fifteen percent of Caucasians lack the $D(Rh_o)$ antigen and are called Rh-negative. When transfused once with Rh-positive blood, Rh-negative persons have about a fifty percent chance of forming anti-$D(Rh_o)$ antibodies, which could cause destruction for any subsequently transfused Rh-positive red blood cells.

There are five additional clinically import antigen systems: the Kidd ($Jk^a$, $Jk^b$), Kell (K,k,Js$^a$), Duffy (Fy$^a$, Fy$^b$), Luthern (Lu$^a$, Lu$^b$), and the MNS (S,s) system. The frequency of all of the phenotypes has been defined in people of Western European and African descent. It is likely that antibodies to all of these antigens may be responsible for red blood cell destruction, albeit at different frequencies.

"Natural" alloantibodies are defined as alloantibodies specific for the blood group antigens that occur in the absence of known stimulus by foreign red blood cells. Nearly all individuals produce "naturally occurring" antibodies against the A or B antigens not present on their own red blood cells. Naturally occurring antibodies tend to be IgM molecules, and many of them (notably excepting anti-A and Anti-B) react poorly at body temperature but readily agglutinate red blood cells at 5°–20° C. The anti-A and anti-B naturally occurring antibodies are used as the basis for confirming the red blood cell type.

A second type of antibodies is termed "immune antibodies." These alloantibodies are formed in response to another person's red blood cells or soluble blood group. The antibodies initially belong to the IgM subclass but usually change to IgG class within a few weeks or months. An example of "immune antibodies" are those antibodies formed when Rh-negative persons are transfused with Rh-positive blood.

An "electronic fluorescent-activated cell sorter" (FACS) is a device which separates (or analyses the composition of) individual cells traveling in single file in a fine stream. The cells are assessed for their fluorescence by passing them through a laser beam. If desired, tiny droplets, most containing one or no cells, are formed by a vibrating device. The droplets containing single cells are automatically given a positive or a negative charge at the moment of formation, depending on whether they contain a fluorescent cell; they are then deflected by a strong electric field into an appropriate container. In FACS analyses, when right angle light scattering of incident light is plotted against forward angle light scattering of incident light, the resultant is a series of derivative functions of size. The cells can also be stained prior to FACS analyses. As markers, a wide variety of fluorescent molecules can be employed, which may be conjugated as labels to antibodies specific for cellular markers which identify particular sets and subsets of cells. The antibodies can either be directly conjugated to a fluorochrome, or a primary, unconjugated antibody directed against a cellular antigen can be used first, followed by a second, fluorochrome-labelled antibody direct against the primary antibody. Ligands to receptors may also be conjugated, where the ligands may be naturally occurring or synthetic, proteins, saccharides, synthetic organic molecules or the like, or molecules which bind to other molecules, such as major histocompatibility complex-T cell receptor combinations. Fluorescent dyes which enter the cell itself (e.g. propidium iodide or PKH26) may also be employed. Using current technologies, up to four different fluorescent parameters can be measured on a single cell.

The basis for separation in the flow cytometer depends on the light detectable characteristics of the cell. The parameters of interest are defined as the "gates" used to analyze the cell population of interest. Thus, various light characteristics can be used in the cell sorter, which characteristics include light scatter and fluorescence, where the flow cytometer can detect the effect of the cell on the laser beam.

A "fluorochrome" is a substance which typically and preferably results in a change in the amount of light absorbance (optical density) or emission of the assay medium when excited by energy of the appropriate wavelength. Preferred fluorochromes include, but are not limited to, fluorescein isothiocyanate (FITC), phycoerythrin (PE), duochrome, allophycocyanin (APC), Tandem, or Texas Red. All of these are commercially available.

"Microsphere beads" are defined as a small, spherical solid support that may be detected by flow cytometry techniques. The solid supports preferable will comprise particles of beads having an average diameter of about 0.25 microns to about 100 microns, most preferably 2 microns to about 15 microns. Suitable materials for solid supports include organic polymers, both naturally occurring and synthetic, such as polysaccharides, styrene polymers, polyacrylates (e.g. polyacrylamide, glass, ceramic, carbon, polyvinyl chloride, protein, and the like. Styrene polymers include, but are not limited to, polystyrene, polymers containing aromatic moieties, and higher aromatic compounds such as naphthalene, anthracene, etc. The solid supports may also contain a latex compound (see U.S. Pat. No. 5,567,627).

GENERAL ASPECTS

The components and operation of flow cytometers is well known to those skilled in the art and will not be described in detail herein. For purposes of a description of such applicants refer to U.S. Pat. No. 5,567,627, issued Oct. 22, 1996 which is incorporated herein by reference and to publications describing such. It is sufficient to indicate that the components and methodology of flow cytometry can be used to provide specific information on a number of parameters of a sample. For example it is possible to provide information on components of different sizes within a sample, while simultaneously providing information on signals of different wavelengths received from different components received from the sample. Thus, when a sample includes components of varying sizes and also includes components with labels which emit different wavelengths of light the flow cytometry data obtained can provide multidimensional information to the user. The present invention utilizes this technology by providing different types of labelled antibodies, beads of different sizes attached to known antigens, and labelled and unlabelled cells exhibiting known antigens. By exposing a sample to such and thereafter analyzing such within a flow cytometer it is possible to obtain substantial amounts of information regarding the blood in a quick and efficient manner.

Figure 1A:
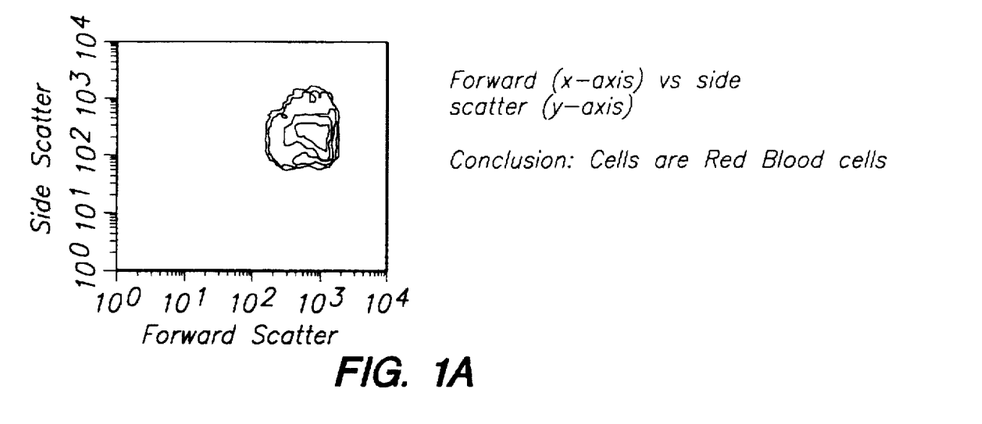
Figure 1B:
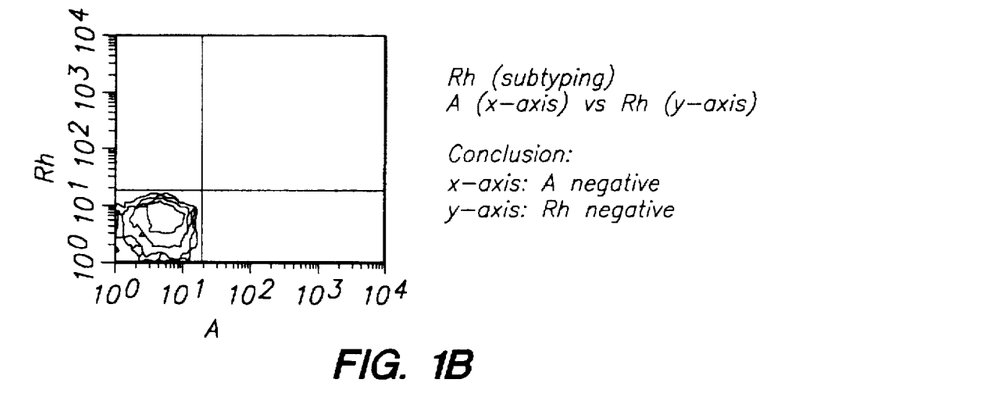
Figure 1C:
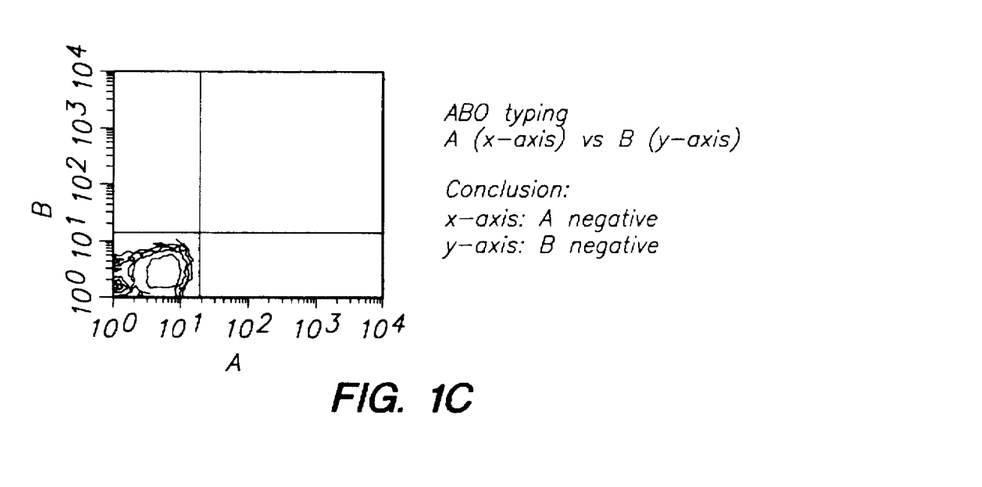
Figure 2A:
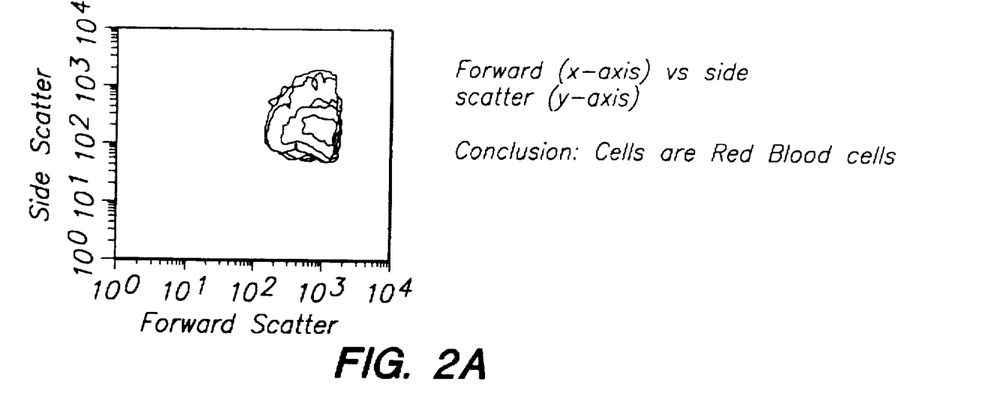
Figure 2B:
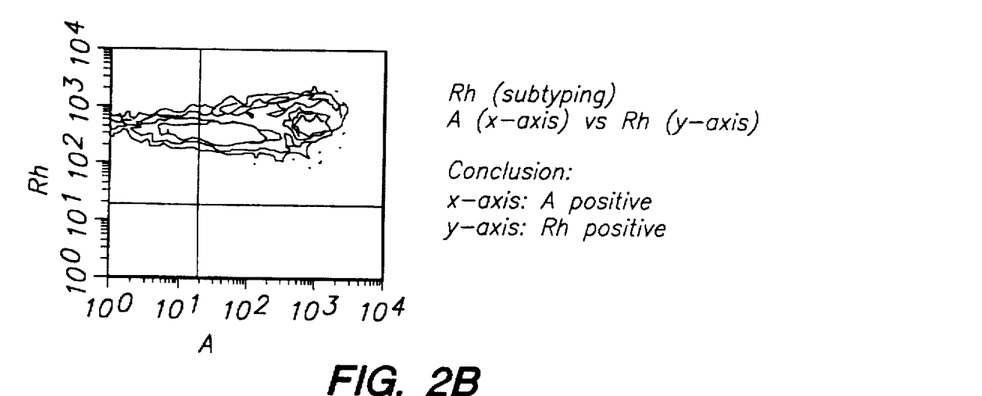
Figure 2C:
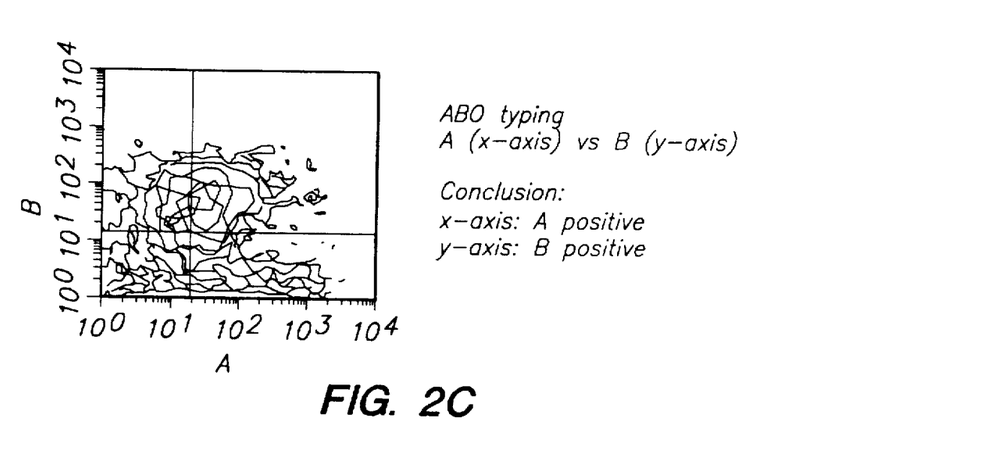

A first analysis is carried out when a blood sample to be analyzed is reacted with anti-A, anti-B and anti-D antibodies wherein each of the antibodies is bound to a detectable label. The antibody may be directly bound to a label or later bound to a label by an anti-antibody such as anti-IgG or anti-IgM. After reacting the sample to be tested with labelled antibodies any antigens within the sample are given time to bind to the antibodies under appropriate binding conditions. Thereafter, unbound antibodies are removed by washing techniques well understood by those skilled in the art. At this point, the antibody labelled sample may be subjected to flow cytometry. The results will indicate if the blood is type A, B, AB, or O and further indicate the D type i.e., if the blood is Rh positive or negative. Results are shown in FIGS. 1 and 2.

Figure 3A:
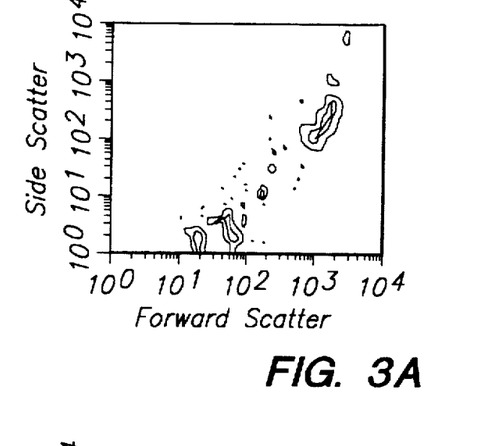
Figure 3B:
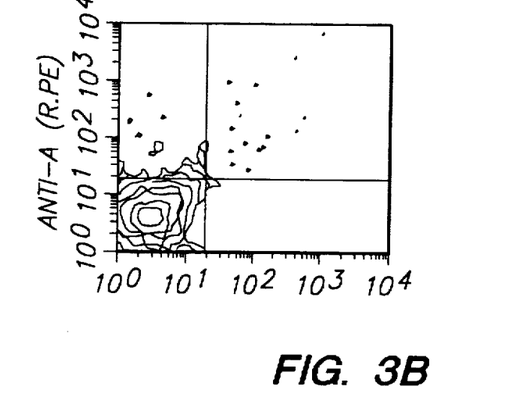
Figure 3C:
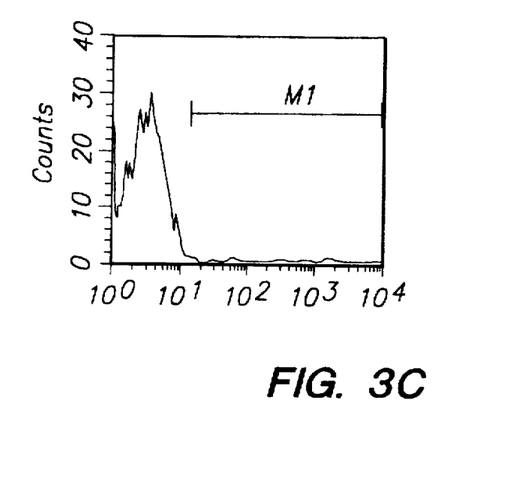
Figure 4A:
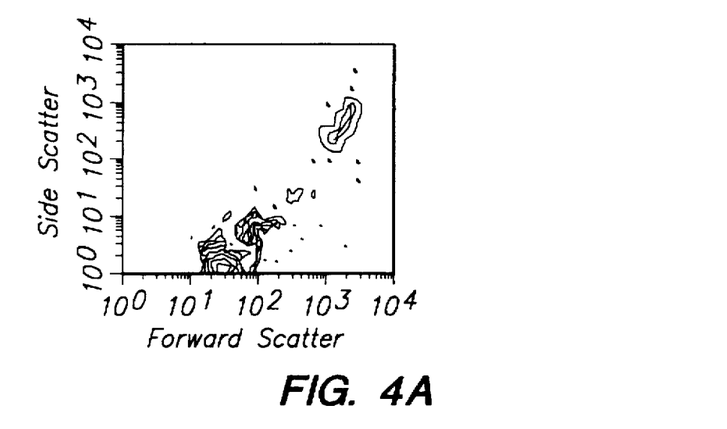
Figure 4B:
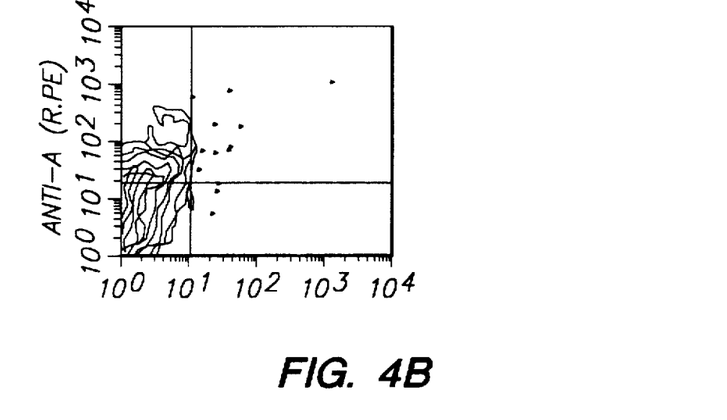
Figure 4C:
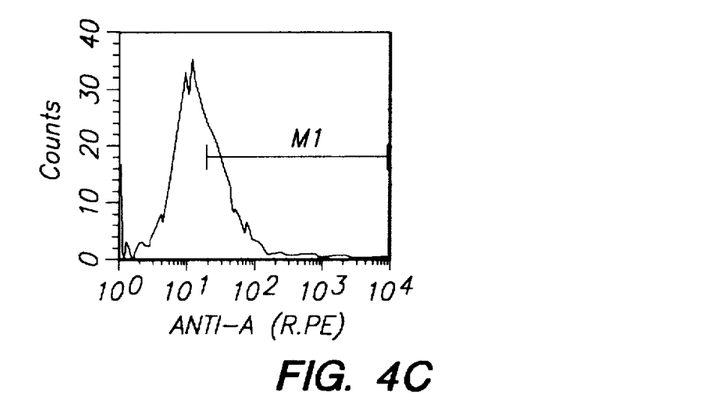

A second analysis may be carried out when prior to washing away unbound antibodies the sample is contacted with beads which beads have on their surface either (1) blood group A antigens or (2) blood group B antigens. However, for the second analysis it is preferable to separately contact the beads with a separate divided portion of the original blood sample. After contacting the blood with the beads the beads are allowed to remain in contact with the blood for a sufficient amount of time such that antibodies within the plasma of the blood will bind to antigens on the beads. It should be pointed out that the antigens may be attached to the beads in any conventional manner. However, with respect to attaching the blood group B antigens it is difficult to directly attach the antigen to the bead surface. Thus, the antigen should be attached via a connecting group, such as a bifunctional organic linking group. Examples of such groups, well known in protein chemistry, include dialdehydes, such as glutaraldehyde and diamines, such as 1,6 diaminohexane (see U.S. Pat. No. 5,567,627). After the beads are allowed to bind to antibodies within the plasma any unbound material is washed away using standard washing procedures known to those skilled in the art. The beads are then brought into contact with labelled anti-antibodies which bind to any antibodies bound to the surface of the antigens on the beads. Thereafter, the beads are subjected to analysis by flow cytometry. In that the beads are of different sizes depending on the antigen on their surface the analysis will reveal which, if either, type of antibody is present within the tested plasma. Results are shown in FIGS. 3 and 4.

A third, and final analysis is then carried out by adding two groups of cells which cells express different human red blood cell antigens on their surface (e.g. D, C, E, c, e, M, N, S, s, $P_1$, $Le^a$, $Le^b$, K, k, $Fy^a$, $Fy^b$, $Jk^a$, and $Jk^b$) in order to detect unexpected antibodies of clinical signifcance. The first group of cells is labelled with a known dye such as an aliphatic fluorescent reporter dye which permeates the cells being used. The second group of cells is not labelled. The cells are allowed to contact the plasma of the original sample for a sufficient time and under suitable conditions to allow the binding of any antibodies within the plasma to antigens on the cell surfaces. After washing away unbound material the cells which may have antibodies bound to their surface are then brought into contact with labelled anti-antibodies such as anti-IgG which anti-antibodies are labelled with a suitable detectable label. The sample is then subjected to flow cytometry in order to determine if the original sample included antibodies of the type which might be generated by the antigens on either or both of the two types of antigen exhibiting cells.

In order to enhance the selectivity of the present invention it is preferable to carry out each of the above-described three different analyses using a separate divided portion of an original blood sample. However, it is possible to treat the sample in a manner such that all three analysis can be simultaneously carried out by flow cytometry or alternatively to carry out the treatment in a manner such that any two of the analyses can be carried out simultaneously. The first, second and third type of analysis are each described below in further detail.

Flow Cytometric Simutaneous ABO and Rh Blood Typing of RBCs

A flow cytometric technique for the simultaneous RBC antigen detection of ABO and Rh blood groups in a single tube is carried out by selecting a panel of monoclonal antibodies in conjunction with three secondary antibodies with different fluorochrome-labels. Mouse and human monoclonal anti-B and anti-D antibodies were used. Further, mouse monoclonal anti-A antibody was also used. Table 1 shows the combination of monoclonal antibodies to RBC antigens and the corresponding fluorescent-labeled secondary antibodies used.

TABLE 1

ANTIBODIES USED FOR SIMULTANEOUS
FLOW CYTOMETRIC ABO AND Rh DETERMINATION

| Blood Group Antigen | Primary Antibody | Secondary Antibody |
|---|---|---|
| A | Mouse monoclonal IgM | Goat anti-mouse IgM-FITC |
| B | Mouse monoclonal $IgG_1$ | Goat anti-mouse $IgG_1$-TC |
| Rh (D) | Human monoclonal IgG | Goat anti-human IgG-R.PE |

Five parameter (forward scatter, side scatter and three florescence channels) dot plot analyses for simultaneous ABO and Rh determination is presented in FIGS. 1 and 2. A parallel testing of over 300 donor blood specimens from the blood bank including selected weaker variants of $A_2$ and $A_2B$ showed no discrepancies with conventional blood typing.

The flow cytometric method described above can be further refined in a manner which create a no-wash format by directly labelling each of the primary antibodies with one of three different fluorochromes. Automation is feasible in association with filter-bottomed microtiter plates and the Transmed Automated Blood Screening System (TABS), and a computer-controlled robotics sample processor coupled with a flow cytometer.

Flow Cytometric Microphere Immunoassay for Expected Natural Antibodies to RBC Antigen A and B Simultaneous quantitation of multiple analytes in body fluids has been done by using microspheres (beads) of varying size as a solid support for the capture of specific analytes and subsequent immunofluorescent evaluation by flow cytometry (Fulwyler and McHugh, 1990). Those skilled in the art are aware of such flow microsphere immunoassays and immunoreactive bead assays (Scillian, et al., 1989; Yang, et al., 1995). Knowledge relating to such is used for serum antibody screening. Purified blood group antigens A and B are coated onto two different sizes of beads i.e., antigen A on one size beads and antigen B on beads of a different size which size is sufficiently different that flow cytometry can readily discern the difference. The antigen coated beads are employed as a single capture reagent for anti-A or anti-B antibodies naturally present in serum. Incubation of the beads with fluorescent labelled subagglutinating dose of anti-human IgM reveal the binding of specific antibodies upon subsequent analysis of bead size and fluorescence in flow cytometer.

Preliminary results with the beads non-covalently coated with blood group antigen A are shown in FIGS. 3 and 4. A single reagent consisting of different size beads coated with purified blood group substances A and B provides results for natural isoantibodies.

Screening of Serum for Unexpected Antibodies of Clinical Signifigance

Each serum is required to be tested for the occurrence of unexpected antibodies of potential clinical significance using group O reagent RBCs containing most of the antigens against which alloimmune blood group antibodies are reactive. As per the Food and Drug Administration mandate, reagent RBCs used for compatibility testing contain at least the following antigens: D, C, E, c, e, M, N, S, s, $P_1$, $Le^a$, $Le^b$, K, k, $Fy^a$, $Fy^b$, $Jk^a$, and $Jk^b$.

Specific antibody binding to two different pools of reagent Type O red blood cells is discriminated by labelling one set of the red cell population with a fluorescent marker. One of the RBC pools is fluorescent labelled with an aliphatic fluorescent reporter dye such as PKH26. A mixture of labelled and unlabelled reagent RBCs set are incubated with the test serum followed by FITC-anti-human-Ig's. Reactivity of the unexpected antibodies from the serum to a particular set of reagent RBCs is then identified by two color flow cytometric analysis.

Signifigance of the Invention

Comprehensive simultaneous flow cytometric testing of ABO and Rh(D) antigen on the RBCs and anti-A, anti-B antibodies in serum facilitates software-assisted interpretation and reporting of results. Further, the single reagent containing PKH26-labelled screening cells I and unlabelled screening cells II (where cell groups I and II are two distinct populations of type O red blood cells expressing the antigens D, C, E, c, e, M, N, S, s, $P_1$, $Le^a$, $Le^b$, K, k, $Fy^a$, $Fy^b$, $Jk^a$, and $Jk^b$) enable reactions with all clinically significant blood groups that are detected by a single FITC-labelled antigen Ig reagent. In view of such only three tubes are needed to perform both RBC antigen and serum antibody tests.

Recurring reagents' cost can be reduced compared to conventional agglutination tests since fewer reactions are required in the flow cytometric test system. The test system offers excellent precision, sensitivity, speed and objective determination of blood group typing and serum antibody screening. Immunohematologic assays performed in blood collection centers can be automated by this flow cytometric test system.

Experimental

The following example is put forth so as to provide those of ordinary skill in the art with a complete disclosure and description of how to make and carry out the blood analysis of the invention and is not intended to limit the scope of what is regarded as the invention. Efforts have been made to insure accuracy with respect to numbers used (e.g., amounts, temperature, etc.) but some experimental errors and deviations should be accounted for. Unless indicated otherwise, parts or parts by weight, molecular weight is weight average molecular weight; temperature is in degrees centigrade; and pressure is at or near atmospheric.

EXAMPLE 1

In order to simultaneously detect ABO and Rh blood groups by monoclonal antibodies, in conjunction with secondary antibodies conjugated with different fluorochromes, the following assay was performed. Blood samples from approximately 150 volunteer donors were collected from Moffitt Hospital Blood Bank and Irwin Memorial Blood Centers. Rare variants of blood groups were also obtained from Irwin Memorial Blood Centers. A 0.5% suspension of each anti-coagulated human blood sample was prepared in Hemaline (a balanced electrolyte solution). The samples were incubated in 12×75 mm round bottom polystyrene tubes with a mixture of pre-determined optimal dilutions of anti-A (mouse monoclonal IgM, Gamma Biologicals Inc., Texas), anti-B (mouse monoclonal $IgG_1$, (clone BRGL-2, Dr. David J. Anstee, Bristol, United Kingdom), and anti-D (human monoclonal IgG1, clone BRAD-5, Dr. David J. Anstee, Bristol, United Kingdom) in 1 ml Hemaline for 15 minutes at room temperature. The tubes were then centrifuged at 200×g for five minutes. The cells were then washed twice by centrifugation with 1 ml of sheath fluid. The pelleted cells were then resuspended in a mixture of fluorescent labelled second antibodies (goat anti-mouse IgM (human absorbed) F(ab')2-FITC, Caltag Laboratories, South San Francisco, Calif.; goat anti-mouse $IgG_1$, (human absorbed)-TRI-COLOR®, Caltag Laboratories, South San Francisco, Calif.; and goat anti-human $F_c$-specific IgG (mouse absorbed)-phycoerythrin, Caltag Laboratories, South San Francisco, Calif.) and incubated for 30 minutes at room temperature. Following the hybridization period, the cells were washed three times with Hemaline by centrifugation, and were resuspended in 0.5 ml of hemaline for analyses. All samples were analyzed in a Becton Dickinson FACScan flow cytometer, and data were acquired using FACScan Research Software. Data was subsequently analyzed using the LYSYS software program. $O^-$ red blood cells were used as negative control sample for flow cytometry; thus cut-off fluorescence values (gates) were calculated in the analyses of $O^-$ cells. These analyses revealed that parallel testing of all of the samples, including selected weaker variants of $A_2$ and $A_2B$, showed no discrepancies in the ABO and Rh typing. In addition, the $D^u$ variants (Rh typing) were correctly detected. Analyses using the methodology described above were also performed using a reference panel of nine specimens of the rare variants of A and B ($A_3$, $A_x$, $B_3$, $B_m$, $B_x$, $A_1B_w$, and O-A chimera), obtained as red blood cells frozen in liquid nitrogen. In all cases, concordant results with the conventional agglutination tests were obtained.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of analyzing blood, comprising:
   (A) reacting a sample of blood with anti-A, anti-B and anti-D antibodies wherein each of the antibodies is bound to a detectable label;
   (B) contacting a sample of blood with beads having (a) blood group A antigens bound to their surface and (b) blood group B antigens bound to their surface;
   (C) contacting a sample of blood with (a) a first pool of test cells exhibiting human red blood cell antigens which group of test cells are labeled with a detectable label, and (b) a second pool of test cells exhibiting human red blood cell antigens, the second pool of test cells being antigenically distinct from the first pool;
   (D) contacting the first pool and the second pool of test cells with label protein which binds antibodies bound to the surfaces of the first pool and second pool of test cells;
   (E) removing unbound antibodies of (A) and unbound anti-bodies of (D) from the sample;
   (F) subjecting the sample to flow cytometry analysis; and
   (G) analyzing the cytometry analysis to determine (a) ABO and Rh (D) type (b) natural isoantibodies in plasma and (c) alloantibodies in plasma.

2. The method of claim 1, wherein the sample of blood of (A), (B) and (C) is the same undivided sample.

3. The method of claim 1, wherein the sample of blood of (A), (B) and (C) are each a different portion of a sample from a single human patient.

4. The method of claim 1, wherein the sample of any two of (A), (B) or (C) is the same undivided sample.

5. The method of claim 1, wherein the anti-A antibodies comprise mouse monoclonal IgM and goat anti-mouse IgM-FITC; the anti-B antibodies comprise mouse monoclonal IgG, and goat anti-mouse IgG-TC; and the anti-D antibodies comprise human monoclonal IgG and goat anti-human IgG-R.PE.

6. The method of claim 1, wherein the test cells of the first and second pools are human red human red blood cells which exhibit a antigen selected from the group consisting of D, C, E, c, e, M, N, S, s, $P_1$, $Le^a$, $Le^b$, K, k, $Fy^a$, $Fy^b$, $Jk^a$, and $Jk^b$ which antigens bind alloantibodies in plasma.

7. The method of claim 1, wherein the test cells of the first pool are labeled with an aliphatic fluorescent reporter dye.

8. A method of analyzing blood, comprising:

(A) reacting a first portion of a sample of blood with anti-A, anti-B and anti-D antibodies wherein each of the antibodies is bound to a detectable label;

(B) removing unbound antibodies from the sample to obtain an antibody labeled sample;

(C) subjecting the sample to flow cytometry analysis;

(D) analyzing the cytometry analysis to determine ABO and Rh (D) type;

(E) contacting a second sample of a blood with beads having (a) blood group A antigens bound to their surface and (b) blood group B antiantigens bound to their surface;

(F) washing the beads after antibodies in the sample have had an opportunity to bind to the group A and group B antigens;

(G) subjecting the beads to flow cytometry analysis;

(H) analyzing the cytometry analysis to determine if isoantibodies are present in the blood;

(I) contacting a third portion of a sample with test cells exhibiting human red blood cell antigens;

(J) washing the test cells to remove unbound material;

(K) contacting the washed test cells with labeled anti-antibodies;

(L) removing unbound anti-antibodies from the sample;

(M) subjecting the sample to flow cytometry analysis; and (N) analyzing the cytometry analysis to determine if alloantibodies are present in the blood.

9. The method of claim 8, wherein the anti-A antibodies comprise mouse monoclonal $Ig^M$ and goat anti-mouse $Ig^M$-FITC; the anti-B antibodies comprise mouse monoclonal $Ig^G$, and goat anti-mouse $Ig^G$-TC; and the anti-D antibodies comprise human monoclonal $Ig^G$ and goat anti-human $Ig^G$-R.PE.

10. The method of claim 8, wherein the test cells exhibit the antigens D, C, E, c, e, M, N, S, s, $P_1$, $Le^a$, $Le^b$, K, k, $Fy^a$, $Fy^b$, $Jk^a$, and $Jk^b$ which antigens bind alloantibodies in plasma.

11. A blood analysis kit, comprising:

(A) a first container having therein anti-A, anti-B and anti-D antibodies;

(B) a second container having therein labeled anti-antibodies which bind the antibodies of (A);

(C) a third container having therein beads of a first size having blood group A antigens bound to their surface and beads of a second size having blood group B antigens bound to their surface; and (D) a fourth container having therein test cells exhibiting human red blood cell antigens.

12. The kit of claim 11, further comprising:

(E) a fifth container having therein an aliphatic fluorescent reporter dye.

13. The kit of claim 11, wherein the anti-A antibodies comprise mouse monoclonal IgM and goat anti-mouse IGM-FITC; the anti-B antibodies comprise mouse monoclonal IgG, and goat anti-mouse IgG-TC; and the anti-D antibodies comprise human monoclonal IgG and goat anti-human IgG-R.PE.

14. The kit of claim 11, wherein the test cells exhibit the antigens D, C, E, c, e, M, N, S, s, $P_1$, $Le^a$, $Le^b$, K, k, $Fy^a$, $Fy^b$, $Jk^a$, and $Jk^b$ which antigens bind alloantibodies in plasma.

15. A method of transfusing blood, comprising:

(A) reacting a first portion of a sample of blood with anti-A, anti-B and anti-D antibodies wherein each of the antibodies is bound to a detectable label;

(B) removing unbound antibodies from the sample to obtain an antibody labeled sample;

(C) subjecting the sample to flow cytometry analysis;

(D) analyzing the cytometry analysis to determine ABO and Rh (D) type;

(E) contacting a second sample of a blood with beads having (a) blood group A antigens bound to their surface and (b) blood group B antigens bound to their surface;

(F) washing the beads after antibodies in the sample have had an opportunity to bind to the group A and group B antigens;

(G) subjecting the beads to flow cytometry analysis;

(H) analyzing the cytometry analysis to determine if isoantibodies are present in the blood;

(I) contacting a third portion of a sample with test cells exhibiting human red blood cell antigens;

(J) washing the test cells to remove unbound material;

(K) contacting the washed cells with labeled anti-antibodies;

(L) removing unbound anti-antibodies from the sample;

(M) subjecting the sample to flow cytometry analysis;

(N) analyzing the cytometry analysis to determine if alloantibodies are present in the blood; and (O) infusing a fourth portion of the blood sample into a patient with a matching ABO and Rh (D) type as determined in (D) after confirming that the blood does not contain isoantibodies in (H) or alloantibodies in (N).

16. The method of claim 15, wherein the anti-A antibodies comprise mouse monoclonal IgM and goat anti-mouse IgM-FITC; the anti-B antibodies comprise mouse monoclonal IgG, and goat anti-mouse IgG-TC; and the anti-D antibodies comprise human monoclonal IgG and goat anti-human IgG-R.PE.

17. The method of claim 15, wherein the test cells exhibit the antigens D, C, E, c, e, M, N, S, s, $P_1$, $Le^a$, $Le^b$, K, k, $Fy^a$, $Fy^b$, $Jk^a$, and $Jk^b$ which antigens bind alloantibodies in plasma.

18. The method of claim 15, wherein test cells are labeled with an aliphatic fluorescent reporter dye.

* * * * *